United States Patent [19]
Mobin-Uddin et al.

[11] Patent Number: 5,820,585
[45] Date of Patent: Oct. 13, 1998

[54] ANGIOGRAPHIC AND ARTERIOGRAPHIC BALLOON CATHETER

[76] Inventors: Kazi Mobin-Uddin, 483 Delegate Dr., Cols., Ohio 43235; Kenneth R. Blake, 9641 Thomas Ave. N., Brooklyn Park, Minn. 55444

[21] Appl. No.: 658,389

[22] Filed: Jun. 5, 1996

Related U.S. Application Data

[63] Continuation of Ser. No. 415,717, Apr. 3, 1995, abandoned.

[51] Int. Cl.$^6$ .................................................. A61M 31/00
[52] U.S. Cl. ............................... 604/53; 604/49; 604/52; 604/96
[58] Field of Search ................................ 604/96, 97, 98, 604/99, 102, 103, 104, 264, 280, 49, 53, 52

[56] References Cited

U.S. PATENT DOCUMENTS

| | | | |
|---|---|---|---|
| 4,782,834 | 11/1988 | Maguire et al. | 604/96 X |
| 4,784,639 | 11/1988 | Patel | 604/280 X |
| 5,085,635 | 2/1992 | Cragg | 604/96 |
| 5,487,730 | 1/1996 | Marcadis et al. | 604/96 |
| 5,489,264 | 2/1996 | Salo | 604/96 X |
| 5,562,652 | 10/1996 | Davis | 604/96 X |

*Primary Examiner*—Wynn Wood Coggins
*Assistant Examiner*—N. Kent Gring
*Attorney, Agent, or Firm*—Faegre & Benson, LLP

[57] ABSTRACT

A method of obtaining x-rays of blood vessels of the circulatory system involving injection of radiopaque dye using a novel balloon catheter is described. The novel balloon catheter has a tube with two separate lumens, for each conducting a separate fluid flow along the length of the tube. An orifice is provided in each lumen at the proximal end of the tube for separately introducing a fluid flow into each lumen. A distal tip end of the tube has perforations for perfusing fluid flow from only the first lumen to an exterior of the catheter. A balloon, provided proximal of the perforations of the distal tip end of the tube, is in fluid flow communication with only the second lumen to provide selective fluid inflation of the balloon.

4 Claims, 8 Drawing Sheets

ANGIOGRAPHIC AND ARTERIOGRAPHIC BALLOON CATHETER

This is a continuation of application Ser. No. 08/415,717 now filed Apr. 3, 1995, now abandoned.

FIELD OF THE INVENTION

This invention relates to a method of obtaining x-rays of blood vessels of the circulatory system involving injection of radiopaque dye by means of a novel balloon catheter device. More particularly, this invention relates to a method of obtaining such x-rays by injection of radiopaque dye to aortas and/or arteries, such as the abdominal aorta and the arteries of the lower extremities. This invention also relates to a novel balloon catheter device for injection of radiopaque dye into selected locations within blood vessels of the circulatory system.

BACKGROUND OF THE INVENTION

A common medical problem, particularly for patients advancing in age, is atherosclerosis or hardening of the arteries. Atherosclerosis is characterized by the formation of irregularly distributed lipid deposits in the intima of large and medium-sized arteries, which collect to act as blockages or occlusions impeding proper blood flow. Depending on the location of these occluded arteries, circulation of blood is thereby restricted to certain limbs and/or organs of the body.

In the legs, such blockage of circulation may result in pain in the affected leg while walking, which may progress to pain while resting, then to tissue necrosis, and finally, if untreated, to gangrene and subsequent amputation.

Diagnosis of the condition requires x-rays of selected portions of the abdominal aorta and of its arterial branches to the lower extremities in order to determine the precise location of the blockage(s). Once the exact location of the blockage has been identified, treatment of this atherosclerotic condition can be accomplished by arterial bypass surgery, whereby a new unobstructed blood passageway is established around the area of blockage to improve circulation of blood to the affected lower extremity.

DESCRIPTION OF THE PRIOR ART

Figure 1:
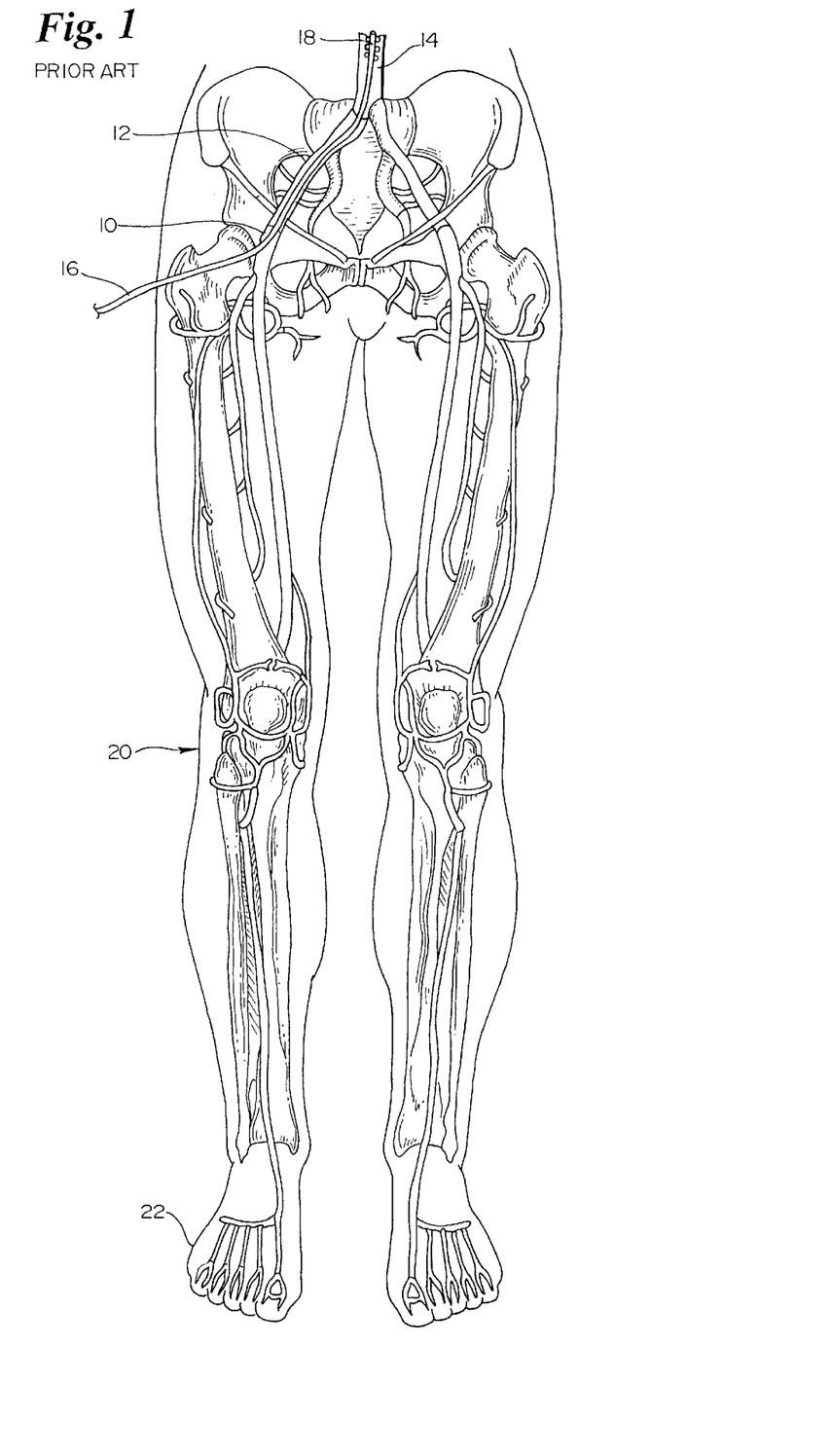
FIG. 1 illustrates a conventional single-lumen linear perfusion catheter with the perforated tip end positioned in the abdominal aorta.
Figure 2:
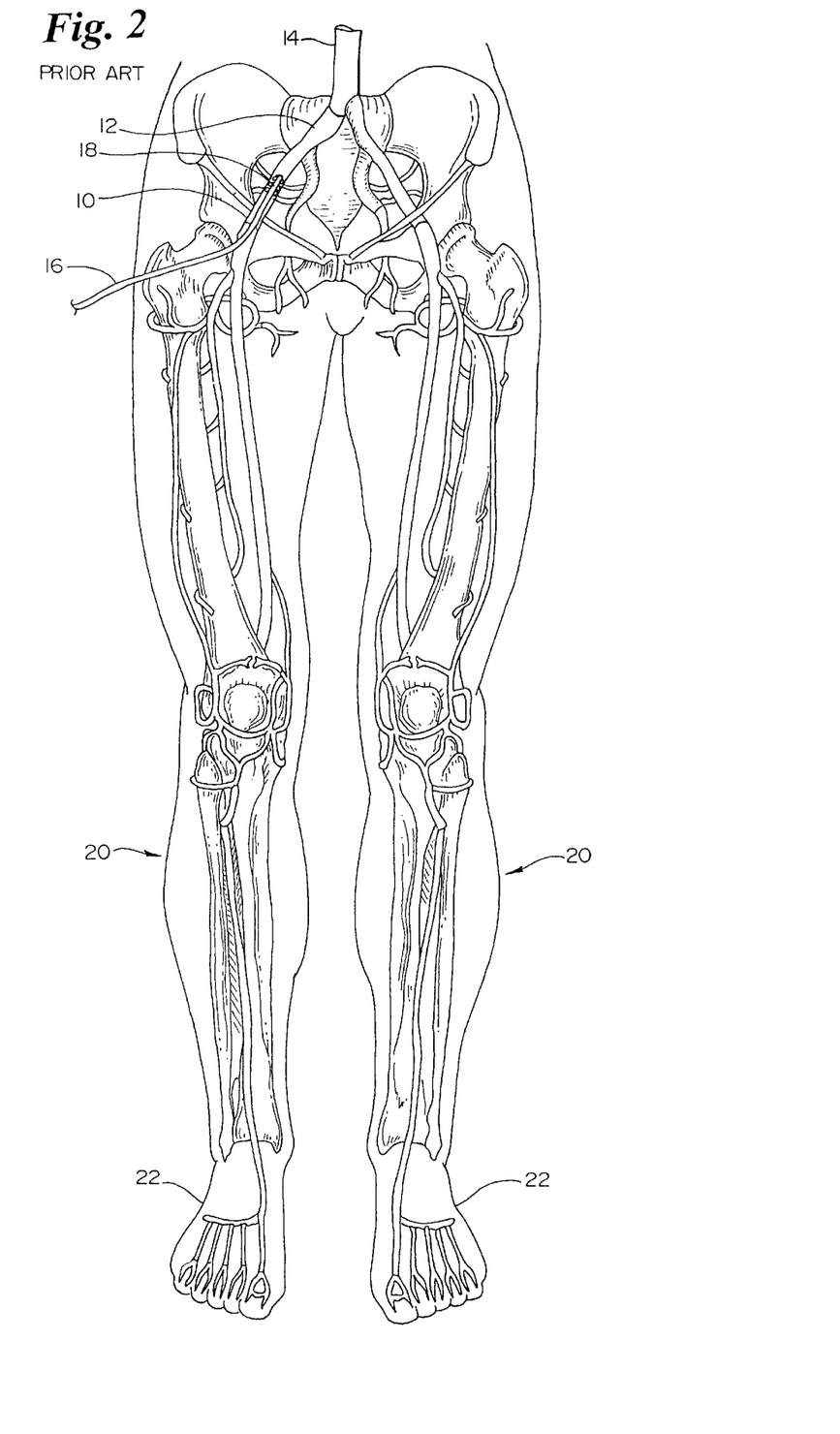
FIG. 2 illustrates a conventional single-lumen linear perfusion catheter with the perforated tip end positioned in the external ipsilateral iliac artery.
Figure 3:
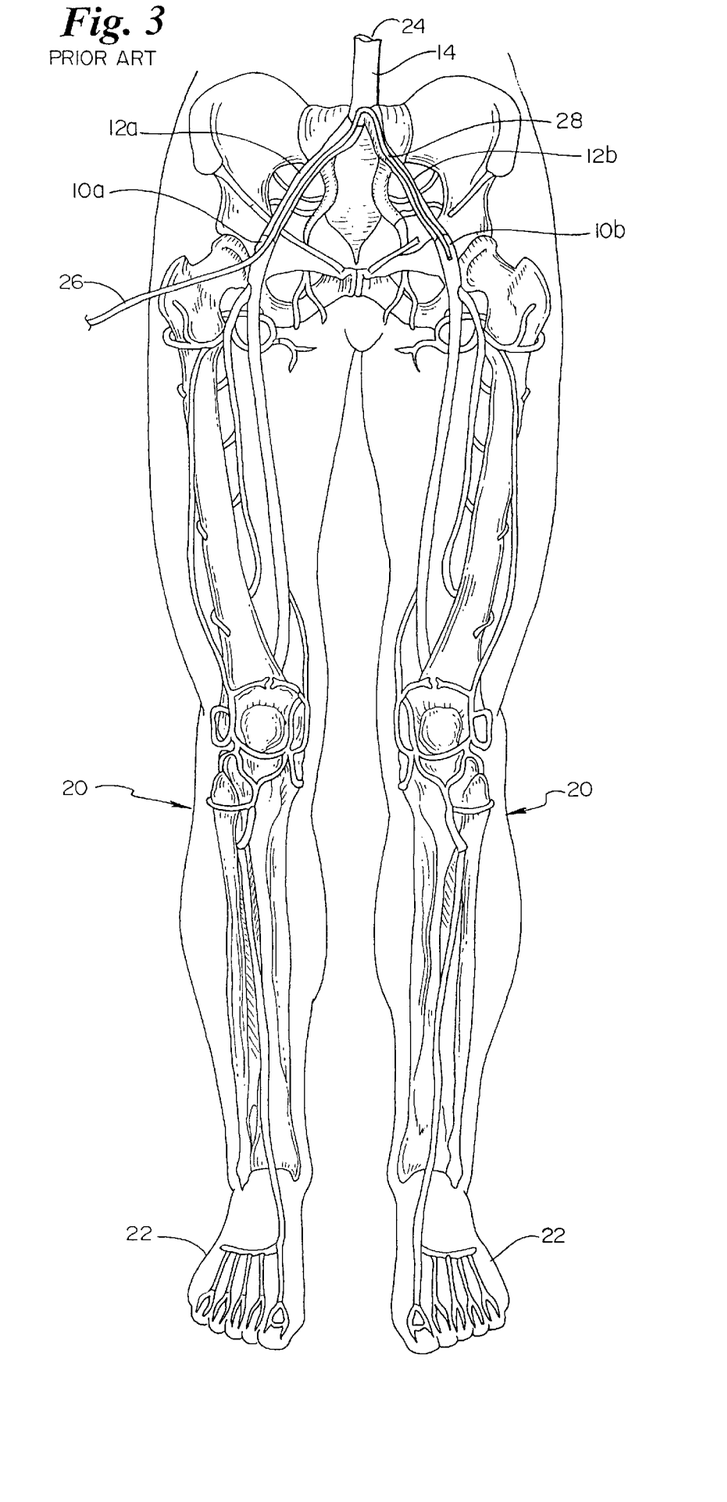
FIG. 3 illustrates a conventional single-lumen non-linear perfusion catheter with a specially formed tip end positioned in the contralateral iliac artery.
Figure 4:
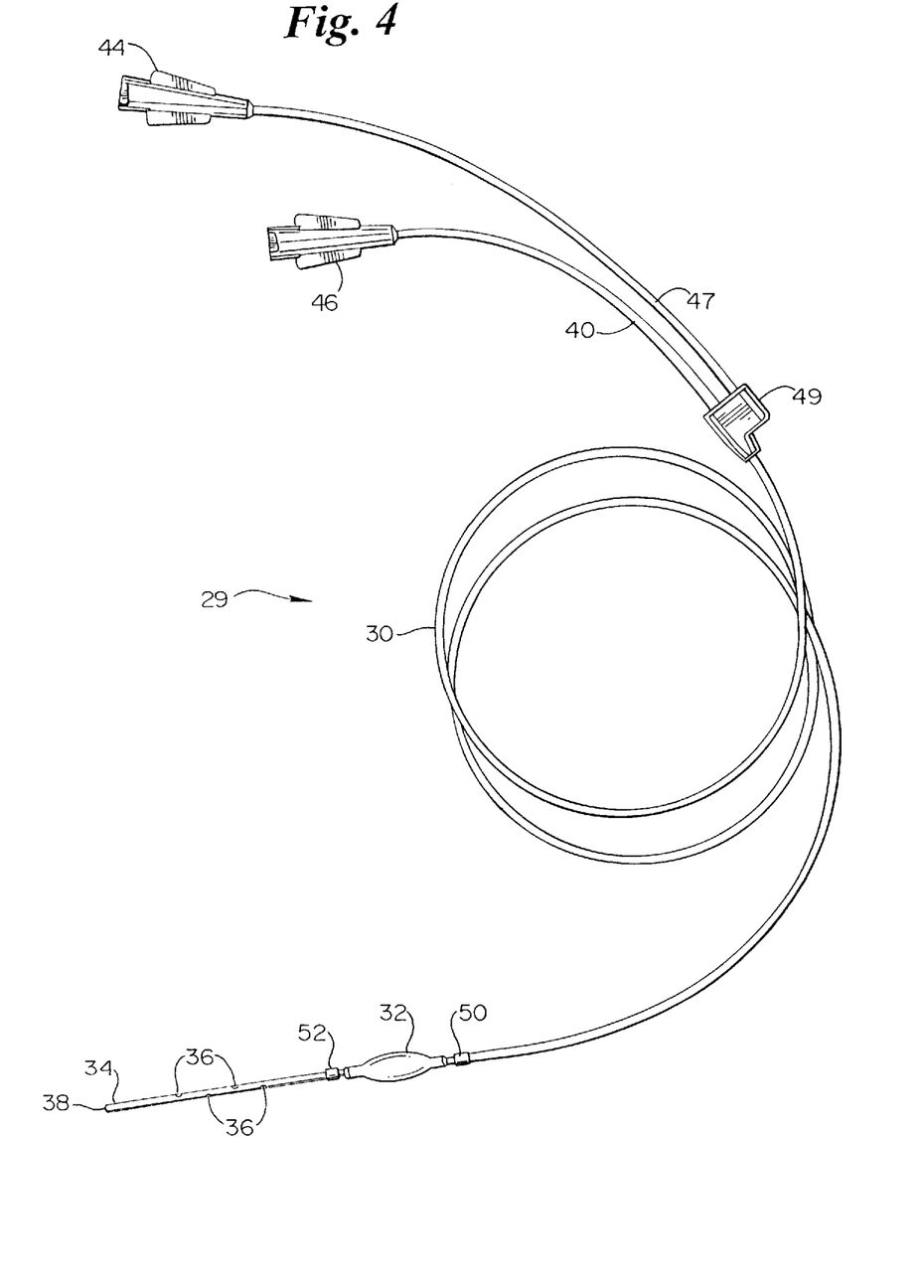
FIG. 4 is a perspective view of the balloon catheter of the present invention.

A conventional method of preparing aortograms and arteriograms with a conventional single-lumen linear dye perfusion catheter will now be discussed with reference to prior art FIGS. 1–3.

BILATERAL AORTOGRAM (PRIOR ART FIG. 1)—An aortogram with distal run-off is performed with reference to prior art FIG. 1 in the following manner:

A needle puncture is made in the common femoral artery 10 and then a guide wire (not shown) is passed through the needle (also not shown) into the femoral artery 10, and the needle is withdrawn. The guide wire is then advanced under fluoroscopic control through the iliac artery 12 into the abdominal aorta 14. A single-lumen linear catheter 16 with a perforated distal tip end 18 is then advanced over the guide wire into the abdominal aorta 14 and the guide wire is withdrawn. X-ray contrast medium is injected into the abdominal aorta 14 through the perforated distal tip end 18 of the catheter 16 to flow through the abdominal aorta 14 and into the iliac 12 and femoral arteries 10 of both lower extremities 20, 22. X-rays of the abdomen and of both lower extremities 20, 22 can then be taken. The abdominal aorta 14 and the arterial system 10, 12 supplying blood to both lower extremities 20, 22 are thus visualized, and any blockage in the aorta 14 and/or the arteries 10, 12 can be identified.

In patients with severe atherosclerotic occlusive disease (that is, extremely large atherosclerotic depositions), following injection of the x-ray contrast medium into the abdominal aorta 14, the volume and concentration of x-ray contrast medium reaching each lower extremity may not be sufficient to visualize the most distal arteries in the leg 20 and foot 22. In such situations, a selective additional injection of the x-ray contrast medium into the iliac artery 12 of each lower extremity 20, 22 is required to facilitate better visualization of the distal arteries in the leg 20 and foot 22.

IPSILATERAL LOWER EXTREMITY ARTERIOGRAM (PRIOR ART FIG. 2)—As illustrated with reference to prior art FIG. 2, the catheter 16 is again initially advanced into the abdominal aorta 14, and then slightly retracted until the distal tip end 18 of the catheter 16 is positioned in the external ipsilateral iliac artery 12. Following injection of x-ray contrast medium in the external ipsilateral iliac artery 12, x-rays of the arteries 10, 12 of the ipsilateral lower extremity are taken.

CONTRALATERAL LOWER EXTREMITY ARTERIOGRAM (PRIOR ART FIG. 3)—In preparation for this type of x-ray, a long guide wire (not shown) is advanced through the single lumen catheter 16 into the thoracic aorta 24 (superior to the abdominal aorta 14), in the manner described with reference to prior art FIG. 2, and the catheter 16 is removed. As illustrated with reference to prior art FIG. 3, a single-lumen non-linear catheter 26 with a pre-formed tip 28 is advanced over the guide wire up into the thoracic aorta 24. The non-linear catheter 26 over the guide wire is then manipulated from the thoracic aorta 24 into the abdominal aorta 14, and into the contralateral iliac artery 12b. The guide wire is then removed. X-ray contrast medium is injected through the non-linear catheter 26 into the contralateral iliac artery 12b and x-rays of the contralateral lower extremity are taken.

Following conclusion of any of the aortograms and/or arteriograms as described with reference to any of prior art FIGS. 1–3, the catheter 16, 26 is retracted and removed from the patient, and pressure is applied in the groin area over the arterial puncture site in the common femoral artery 10 for a time sufficient to control bleeding, usually at least 20 minutes.

Certain disadvantages have been noted with regard to the conventional manner of preparing aortograms and/or arteriograms as described with reference to prior art FIGS. 1–3.

1) For obtaining contralateral lower extremity arteriograms (as described with reference to prior art FIG. 3), a special non-linear catheter 26 is required which must be manipulated up into the thoracic aorta 24, and then retracted into the abdominal aorta 14 and into the contralateral iliac artery 12b. Manipulation of this catheter 26 within the aorta 14, 24 may result in detachment and embolization of atherosclerotic plaques into the lower extremity 20, 22, which may result in further blockage of circulation to the leg and attendant possible loss of limb.

2) Highly skilled technique is required to manipulate the non-linear catheter 26 from the ipsilateral femoral artery 10a to the contralateral iliac artery 12b.

3) The catheter 16 for injecting x-ray contrast medium for an aortogram and/or arteriogram is usually inserted via the femoral artery 10 of the symptomatic leg, as it is easier to do a selective injection of the lower extremity by slightly retracting the catheter 16 from the abdominal aorta 14 into the external iliac artery 12. Following removal of either catheter 16 or 26, there is always leakage of blood from the arterial puncture site into the surrounding tissues. Normal tissue planes are destroyed, making dissection of the femoral artery 10 more difficult at surgery. Moreover, sometimes during surgical dissection of the femoral artery 10, the fresh arterial puncture site re-opens and starts bleeding. Proximal control and suture ligation of the puncture in the femoral artery 10 are then required to control bleeding.

SUMMARY OF THE INVENTION

A balloon catheter according to the present invention is comprised as follows:

The catheter has a tube with a first and a second lumen, each lumen adapted and arranged for conducting a separate fluid flow from a proximal end to a distal end of the tube.

An orifice is provided in each lumen at the proximal end of the tube for introducing a separate fluid flow into each lumen.

A distal tip end of the tube is provided with perforations for perfusing fluid flow only from the first lumen to an exterior of the catheter.

A balloon is provided proximal of the perforations of the distal tip end of the tube, adapted and arranged so that the balloon is in fluid flow communication only with the second lumen to provide selective fluid inflation of the balloon.

A method of obtaining an x-ray of a blood vessel using a balloon catheter according to the present invention is comprised as follows:

A distal tip end of the balloon catheter according to the present invention is introduced into and positioned within the desired blood vessel.

X-ray contrast medium is perfused through the distal tip end of the catheter into the blood vessel, and an x-ray of the blood vessel is taken to visualize the area perfused by the x-ray contrast medium.

Alternatively, once the balloon of the catheter of the present invention has been positioned within a blood vessel, the balloon is inflated prior to perfusing the x-ray contrast medium, thereby perfusing contrast medium within the blood vessel only distal of the balloon.

DETAILED DESCRIPTION OF THE INVENTION

The novel balloon catheter 29 of this invention is suitable for use in preparation of blood vessels for aortograms and arteriograms, and especially in preparation for ipsilateral and contralateral selective lower extremity arteriograms.

The novel balloon catheter 29, as illustrated in FIGS. 4–11, is formed with double lumen catheter tubing 30, and has a balloon 32 attached to the catheter tubing 30 approximately 2 inches from its distal tip end 34. When inflated, the balloon 32 is able to be expanded to a maximum of about 22 mm in diameter. The tubing 30 is preferably formed of a biologically benign material. Suitable tubing for this purpose is readily commercially available. Typically, the tubing 30 is size 4 or 5 French.

The balloon 32 is preferably formed of a biologically benign material. A suitable balloon for this purposed is readily commercially available. As can be seen in FIGS. 8–11, the first lumen 40 and the second lumen 42 are parallel to each other within the tubing 30. The first lumen 40 is of slightly larger diameter and provides fluid flow communication from a first fluid fitting 44 at a proximal end of the balloon catheter 29 to the distal tip end 34 for transport of x-ray contrast medium. The second lumen 42 is of slightly smaller diameter. Fluid flow communication from a second fluid fitting 46 at a proximal end of the balloon catheter 29 is provided along a length of single lumen tubing 47 through a Y-joint fitting 49 to join to the second lumen 42 through aperture 51. Fluid flow communication is thus provided from the second fluid fitting 46 to a point within the balloon 32 for transport of balloon inflating fluid. Suitable fluid fittings 44, 46 are preferably formed of a biologically benign material and are readily commercially available.

A suitable Y-joint fitting 49 is preferably formed of a biologically benign material. Suitable fittings for this purpose are readily commercially available. Access for the balloon inflating fluid to the interior of the balloon 32 is provided by an aperture 48 from the exterior of the catheter only to the second lumen 42. The remaining length of the second lumen 42 proximal of the aperture 51 and distal of the aperture 48 is filled with a suitable polymeric, material compatible with the material of the tubing, which sets up to occlude the second lumen 42 and to prevent balloon inflating fluid from returning to the proximal tip end to fitting 44 and from reaching the distal tip end 34 of the catheter 29. The terminal 1½ inches of the distal tip end 34 of the catheter tubing 30 distal of the balloon 32 has holes 36 placed circumferentially around the tubing 30 providing fluid flow communication with only the first lumen 40 to permit injection of x-ray contrast medium. The catheter tubing 30 has an open end-hole 38, so that the tubing 30 can be advanced into position within a blood vessel over a guide wire (not shown). To facilitate identification of the position of the balloon 32 within the body, the proximal 50 and the distal end 52 of the balloon 32 is marked with a radiopaque print ink. Suitable ink is readily commercially available.

Figure 5:
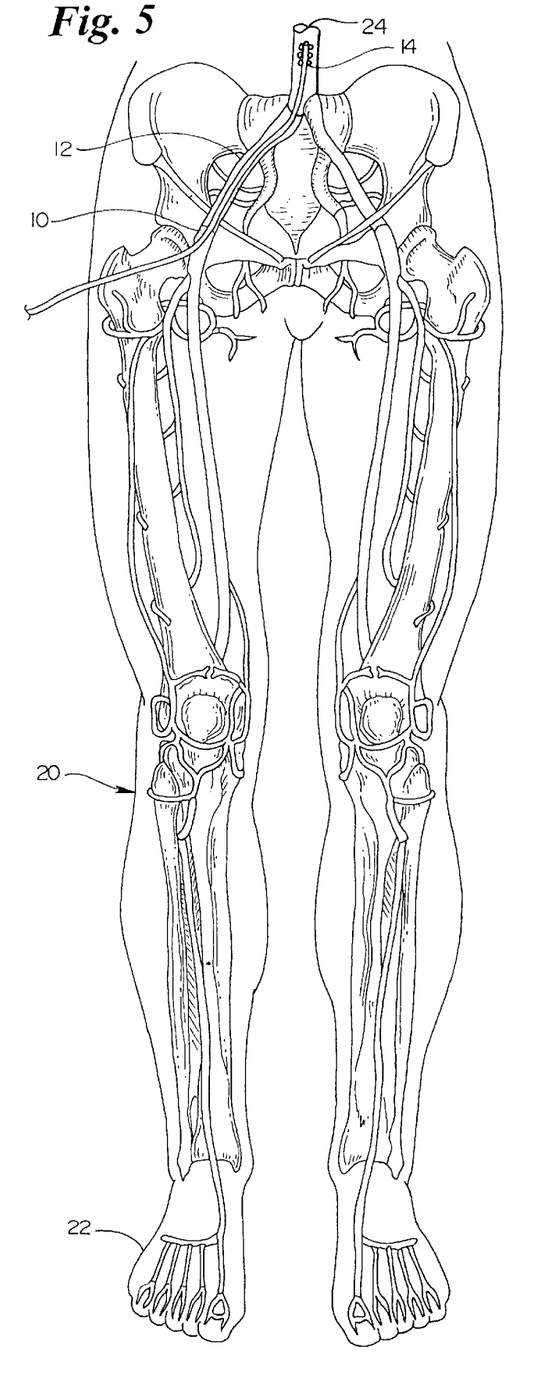
FIG. 5 illustrates the balloon catheter of the present invention with the perforated distal tip end positioned in the abdominal aorta.

As illustrated with reference to FIG. 5, an aortogram is performed using the balloon catheter 29 in the following manner. Following arterial puncture of the common femoral artery 10 with a needle, a guide wire (not shown) is inserted via the needle into the common femoral artery 10. The needle is then withdrawn. The guide wire is advanced into the abdominal aorta 14 under fluoroscopic control.

The balloon catheter 29 is then advanced over the guide wire until the distal tip end 34 is positioned in the abdominal aorta 14 and the guide wire is removed. An abdominal aortogram is made by injecting contrast material into the abdominal aorta 14. The lower extremity x-rays are also taken to demonstrate run-off arteries 10, 12 in both lower extremities 20, 22.

Figure 6:
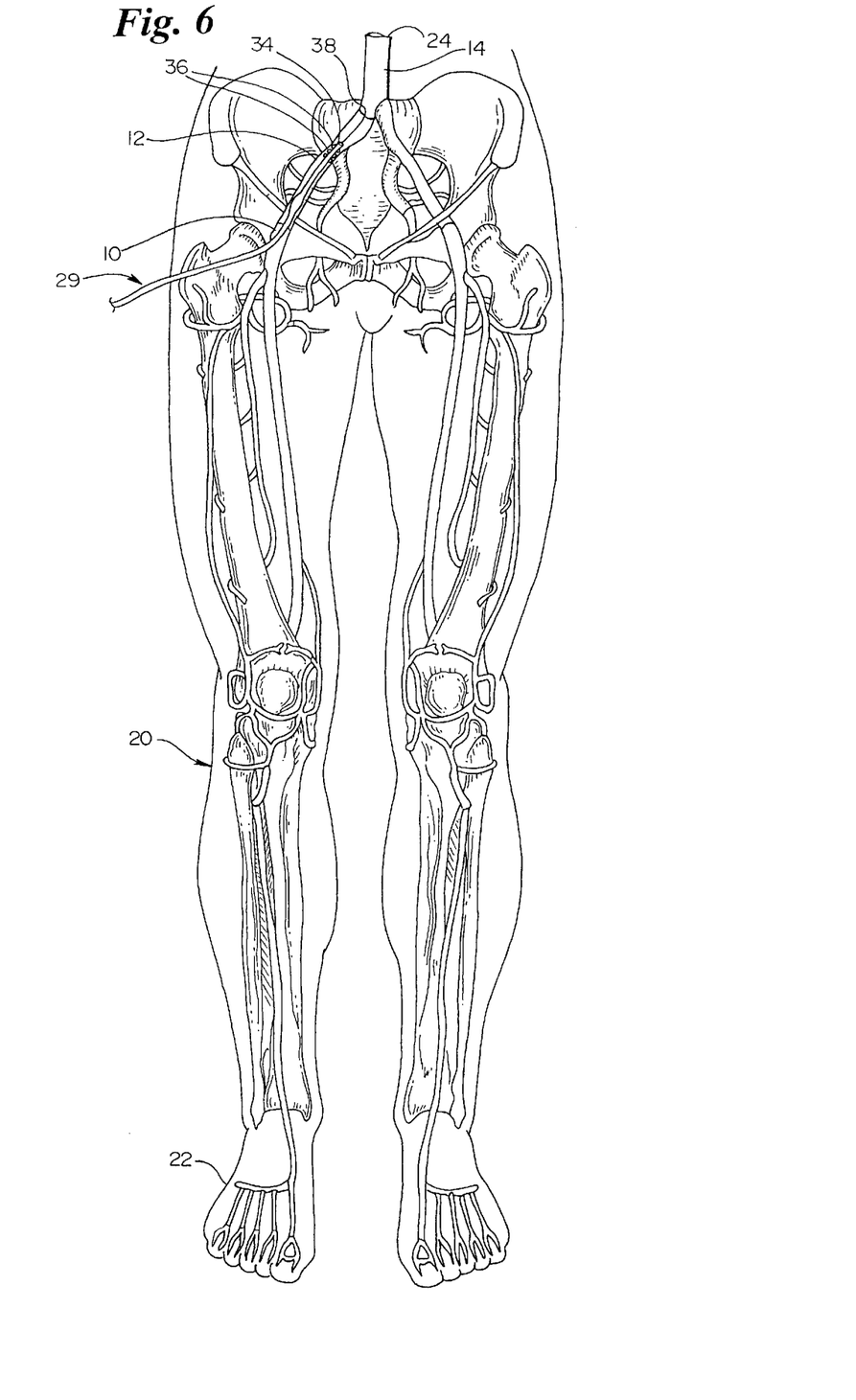
FIG. 6 illustrates the balloon catheter of the present invention with the perforated distal tip end positioned in the external ipsilateral iliac artery.

The use of the balloon catheter 29 for performing a selective ipsilateral lower extremity arteriogram is illustrated with reference to FIG. 6. As described with reference to FIG. 5 above, the catheter 29 is advanced over a guide wire (not shown) into the abdominal aorta 14 and the guide wire is removed. The catheter 29 is then slightly retracted, until its distal tip end 34 is positioned in the external iliac artery 12. With the distal tip end 34 in this position, when x-ray contrast medium is injected, it will flow predominantly through the ipsilateral iliac artery 12 and the femoral artery 10. X-rays of the lower extremity 20, 22 are then taken.

Figure 7:
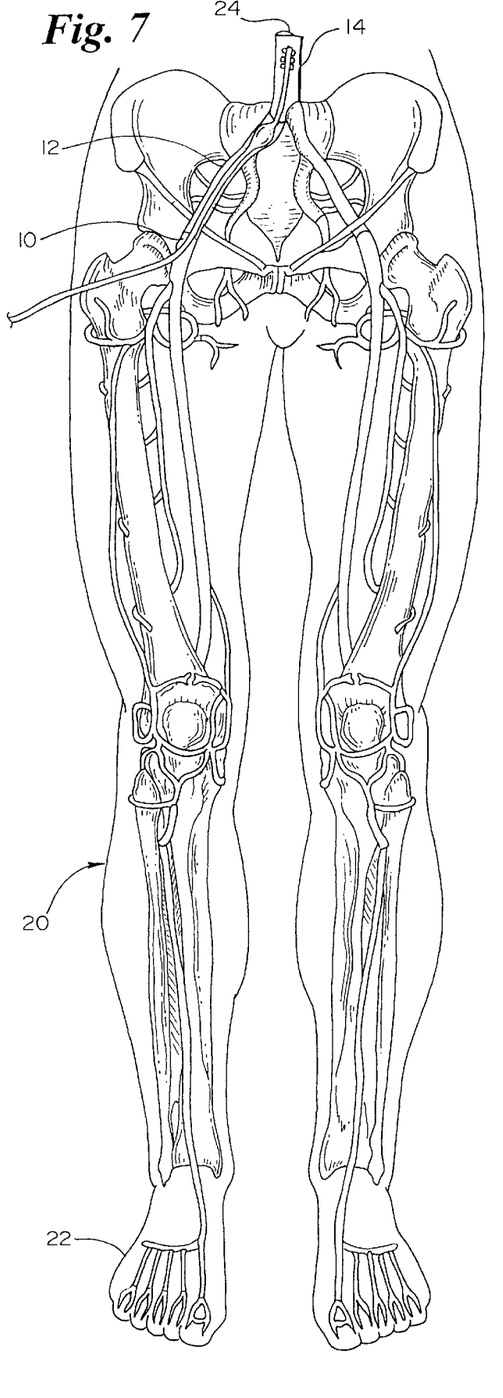
FIG. 7 illustrates the balloon catheter of the present invention with the perforated distal tip end positioned in the abdominal aorta and the inflated balloon positioned in the ipsilateral iliac artery.
Figure 8:
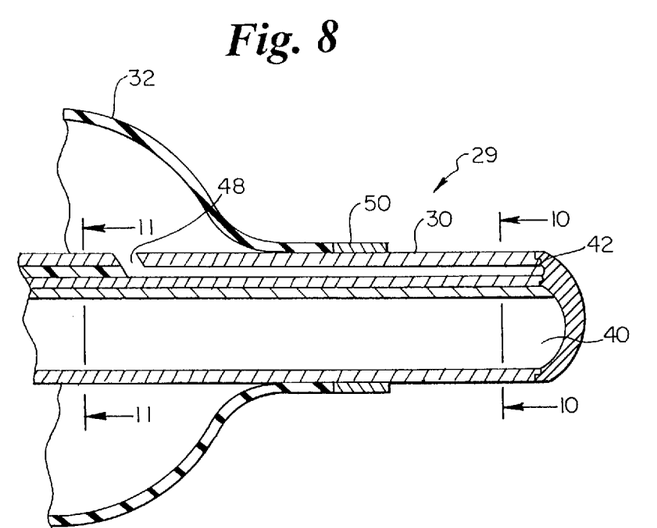
FIG. 8 is a cut-away profile of the balloon catheter of this invention showing the internal structure of the catheter and the balloon.
Figure 9:
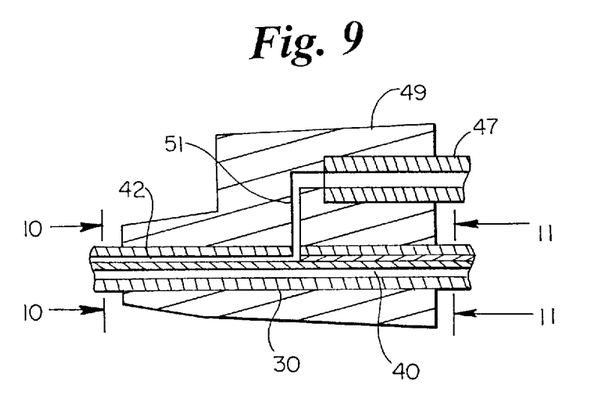
FIG. 9 is a cut-away profile of the balloon catheter of this invention showing the internal structure of the Y-joint joining the two separate fluid introduction sources.
Figure 10:
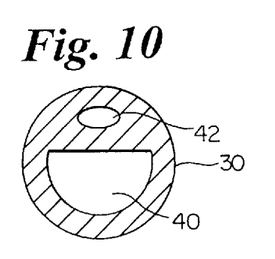
FIG. 10 is a cross-section of FIGS. 8 and 9, taken along lines 10—10.
Figure 11:
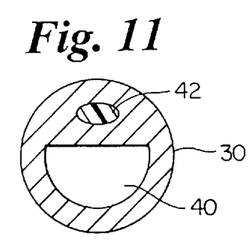
FIG. 11 is a cross-section of FIGS. 8 and 9, taken along lines 11—11.

The use of the balloon catheter 29 for performing a selective contralateral lower extremity arteriogram is illustrated with reference to FIG. 7. The catheter 29 is positioned in the lower abdominal aorta 14, so that the distal tip end 34 is situated immediately above the iliac bifurcation and the balloon 32 is positioned in the common iliac artery 12. Just prior to injection of the x-ray contrast material, the balloon 32 in the iliac artery 12 is inflated to occlude the lower portion of the ipsilateral iliac artery 12a. All of the dye delivered through the distal tip end 34 flows to the lower abdominal aorta 14 and to the contralateral iliac 12b and femoral artery 10b, so that x-rays of the contralateral lower extremity 20, 22 can be taken.

Following completion of the dye injection, the balloon 32 is deflated to restore circulation to the leg 20, 22. The balloon catheter 29 is removed from the patient and pressure is applied to the groin area for time sufficient to control bleeding, usually about 20 minutes.

Some of the advantages to the use of the balloon catheter 29 of the present invention as compared to the prior art catheter, described above with reference to FIGS. 1–3, are as follows.

1) A single catheter 29 can be used to perform aortography and selective ipsilateral and contralateral lower extremity arteriograms.

2) No manipulation of the catheter 29 in the thoracic aorta 24 and the abdominal aorta 14 is required for making a contralateral lower extremity arteriogram, thus avoiding any dangerous migration of atherosclerotic plaque emboli into the lower extremity.

3) To keep the surgical field clear of any extravasated blood, the catheter 29 for the arteriogram is inserted via the femoral artery of the non-symptomatic leg.

4) Services of a highly skilled radiologist may not be necessary, as skilled manipulation of the catheter is not required.

What is claimed is:

1. A method of obtaining an x-ray of a blood vessel comprising:

introducing and advancing a distal tip end of a catheter into the blood vessel, the catheter comprising;
    a tube of size from about 4 to 5 french and having a proximal end portion, a distal end portion with a sidewall, a distal tip, and at least first and second lumens extending through the tube;
    an orifice in each of the lumens at the proximal end portion of the tube for separately introducing fluid into each of the lumens;
    an expansion balloon approximately 2 inches from the distal tip, the balloon being in fluid communication with the second lumen and inflatable in response to fluid flow to occlude an artery; and
    a plurality of perfusion apertures through the tube at locations distal to the balloon, the apertures circumferentially and longitudinally spaced in the sidewall of the distal end portion of the tube and in fluid communication with the first lumen such that placement of the catheter into an artery, inflation of the expansion balloon to occlude the artery, and diffusion of a fluid from the first lumen through the perfusion apertures introduces the fluid to a region of the artery distal to the balloon;

perfusing fluid inflating medium to inflate the balloon;

perfusing an x-ray contrast medium through the first lumen of the catheter into the blood vessel after perfusing fluid inflating medium to inflate the balloon so that the contrast medium is perfused into the blood vessel only distal of the balloon; and taking an x-ray of the blood vessel.

2. The method of claim 1 wherein:

the step of introducing and advancing a distal tip end of the catheter into the blood vessel includes introducing the distal tip end of the catheter into a common femoral artery and advancing the distal tip end through a common iliac artery to a lower abdominal aorta;

the step of perfusing an x-ray contrast medium through the first lumen of the catheter includes perfusing an x-ray contrast medium through the first lumen of the catheter into the common femoral artery and the common iliac artery to the lower abdominal aorta; and the step of taking an x-ray includes taking an aortogram of an area perfused by the x-ray contrast medium.

3. The method of obtaining an x-ray of a blood vessel of claim 1 wherein:

the step of introducing and advancing a distal tip end of the catheter into the blood vessel includes introducing the distal tip end of the catheter into a common femoral artery and advancing the distal tip end to an external iliac artery;

the step of perfusing an x-ray contrast medium through the first lumen of the catheter includes perfusing an x-ray contrast medium through the first lumen of the catheter into the common femoral artery and the external iliac artery; and the step of taking an x-ray includes taking a selective ipsilateral lower extremity arteriogram of an area perfused by the x-ray contrast medium.

4. A method of obtaining a selective contralateral lower extremity arteriogram comprising:

introducing a distal tip end of a catheter into a common femoral artery, the catheter comprising;
    a tube of size from about 4 to 5 french and having a proximal end portion, a distal end portion with a sidewall, a distal tip, and at least first and second lumens extending through the tube;
    an orifice in each of the lumens at the proximal end portion of the tube for separately introducing fluid into each of the lumens;
    an expansion balloon approximately 2 inches from the distal tip, the balloon being in fluid communication with the second lumen and inflatable in response to fluid flow to occlude an artery, and
    a plurality of perfusion apertures through the tube at locations distal to the balloon, the apertures circumferentially and longitudinally spaced in the sidewall of the distal end portion of the tube and in fluid communication with the first lumen such that placement of the catheter into an artery, inflation of the expansion balloon to occlude the artery and diffusion of a fluid from the first lumen through the perfusion apertures introduces the fluid to a region of the artery distal to the balloon;

advancing the distal tip end of the catheter through an ipsilateral iliac artery to a lower abdominal aorta just above an iliac bifurcation, so that the balloon is positioned in the ipsilateral iliac artery;

perfusing a fluid inflating medium to inflate the balloon, thereby preventing fluid flow communication to the ipsilateral iliac artery and the common femoral artery proximal of the balloon;

perfusing an x-ray contrast medium through the catheter into the lower abdominal aorta and a contralateral iliac artery and a contralateral femoral artery; and taking an arteriogram of an area perfused by the x-ray contrast medium.

* * * * *